United States Patent [19]

Beck et al.

[11] 4,346,094

[45] Aug. 24, 1982

[54] 3-ARYL-5-ISOTHIAZOLECARBOXYLIC ACIDS AND RELATED COMPOUNDS USED TO LOWER URIC ACID LEVELS

[75] Inventors: James R. Beck; Robert P. Gajewski, both of Indianapolis; Ronald E. Hackler, Greenfield, all of Ind.

[73] Assignee: Eli Lilly and Company, Indianapolis, Ind.

[21] Appl. No.: 189,435

[22] Filed: Sep. 22, 1980

[51] Int. Cl.$^3$ ................. C07D 275/02; A61K 31/425; A61K 31/44

[52] U.S. Cl. .................................. 424/270; 548/206; 548/213; 548/214; 424/263

[58] Field of Search ...................... 548/206, 213, 214; 424/270

[56] References Cited

U.S. PATENT DOCUMENTS 3,464,999  9/1969  Lemieux et al. .................... 548/206
3,652,575  3/1972  Hutton et al. ....................... 424/270
3,661,920  5/1972  Hepworth et al. ................. 544/133

OTHER PUBLICATIONS

Beringer, et al.; *Chem. Abst.* 66, No. 37820f (1967).
Erlenmeyer, et al.; *Chem. Abst.* 68, No. 83931g (1968).
Burger, Alfred, *Medicinal Chemistry,* Interscience Publishers, Inc., New York, N.Y.; pp. 42, 43 (1960).
Howe, et al., *J. Org. Chem.,* 43, 3736 (1978).
Gewald and Bellman, *Ann.* 1534 (1979).
Howe, et al., *J. Org. Chem.* 43, 3742 (1978).

*Primary Examiner*—Glennon H. Hollrah
*Assistant Examiner*—G. Hendricks
*Attorney, Agent, or Firm*—James L. Rowe; Arthur R. Whale

[57] ABSTRACT

3-Phenyl (or meta or para-substituted phenyl)-4-permissibly substituted-5-isothiazolecarboxylic acids, salts, esters and simple amides, used to lower uric acid levels in mammals.

18 Claims, No Drawings

3-ARYL-5-ISOTHIAZOLECARBOXYLIC ACIDS AND RELATED COMPOUNDS USED TO LOWER URIC ACID LEVELS

BACKGROUND OF THE INVENTION

According to the *Merck Manual*, 12th Edition (D. N. Holvey, M.D., Editor—1972), gout is a recurrent acute arthritis of peripheral joints affecting chiefly mature males and resulting from the deposition in and about the joints and tendons of crystals of monosodium urate. Sodium urate deposits in these places because the patient is hyperuracemic; i.e., his serum levels of urate are elevated to a point at which the solubility of sodium urate is exceeded. Acute attacks of gouty arthritis are treated by the use of an anti-inflammatory drug. The use of colchicine prophylactically will prevent further acute attacks of gout. Uricosuric drugs such as probenecid and sulfinpyrazone can be employed to maintain the serum urate concentration within the normal range.

An alternate method of treatment of gout involves the use of drugs which block the production of uric acid in the mammalian body by blocking the enzyme xanthine oxidase which enzyme converts both hypoxanthine to xanthine and xanthine to uric acid. One such drug is allopurinol (4-hydroxypyrazolo[3,4-d]pyrimidine), an isomer of hypoxanthine. Xanthine oxidase converts this drug to alloxanthine. The competitive conversions of hypoxanthine to xanthine and xanthine to uric acid are thus inhibited and uric acid does not accumulate in the blood. Allopurinol treatment has the further advantage of dissolving uric acid from tophi. Because of its different mechanism of action, allopurinol does not interfere with the effectiveness of the uricosuric drugs, probenecid and sulfinpyrazone, nor with the use of colchicine. Not all patients are able to tolerate allopurinol, however, and it is an object of this invention to provide a drug having the desirable properties of allopurinol without some of its undesirable side effects.

3-Aryl-5-isothiazolecarboxylic acids are known. For example, Naito et al., *Chem. Pharm. Bull.*, 16, 148 (1960) reacted 3-phenyl-4-bromo-5-isothiazolyl lithium with dimethylformamide to yield 4-bromo-5-formyl-3-phenylisothiazole which compound could be oxidized to yield 3-phenyl-4-bromo-5-isothiazolecarboxylic acid. 3-Phenyl-5-isothiazolecarboxylic acid also has been prepared on several occasions. Beringer et al., *Helv. Chim. Acta.*, 49, 2466 (1966) prepared 3-phenylisothiazole from 3-phenyl-5-aminoisothiazole via a diazonium salt. 3-Phenylisothiazole, on treatment with butyllithium followed by treatment with carbon dioxide, yielded 3-phenyl-5-isothiazolecarboxylic acid. Erlenmeyer et al., Ibid, 51, 39 (1968) measured the stability constants of certain acids including 3-phenyl-5-isothiazolecarboxylic acid. Frann and Black, *Tetrahedron Letters*, 1381 (1970) found that a reaction of 5-phenyl-1,3,4-oxathiazol-2-one and two molar equivalents of ethyl propiolate yielded a mixture of the isomeric esters, ethyl 3-phenyl-4-isothiazolecarboxylate and ethyl 3-phenyl-5-isothiazolecarboxylate. Howe et al., *J. Org. Chem.*, 43, 3732–3736 (1978) prepared mixtures of the same two isothiazole esters carrying at the 3-position a m-trifluoromethylphenyl group, a phenyl group, a 4-chlorophenyl group, a 4-cyanophenyl group and a 3,5-dimethoxyphenyl group. Ethyl 3-phenyl-5-isothiazolecarboxylate and the corresponding methyl ester are disclosed in *J. Org. Chem.*, 44, 510 (1979). Methyl 3-phenyl-4-amino-5-isothiazolecarboxylate and the corresponding ethyl ester are disclosed in a paper by Gewald and Bellmann, *Ann.*, 1534 (1979). In none of the above publications is there any reference to a pharmacological action for any of the isothiazolecarboxylic acids or esters described therein and in particular there is no disclosure of any xanthine oxidase activity possessed by such acids or esters.

SUMMARY OF THE INVENTION

This invention provides a method for lowering the urate (uric acid) level in the blood of mammals by the administration to a mammal having elevated urate blood levels via the oral route, an effective amount of a compound of the following formula

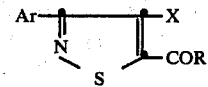

wherein
Ar is pyridyl, thienyl, phenyl or

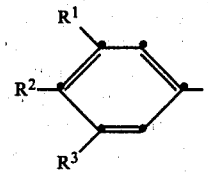

wherein $R^1$, $R^2$ and $R^3$ are individually H, $CF_3$, hal, alk or O-alk or $R^1$ and $R^2$ or $R^2$ and $R^3$ when taken together are methylenedioxy;
X is $NH_2$, H, hal, OH or NH-alk;
R is OH, OM, O-alk, $NH_2$, NH-alk or N(alk)$_2$; wherein hal is Cl, F, I, or Br; alk is ($C_1$–$C_3$) alkyl; and M is a non-toxic cation, preferably an alkali metal cation such as K or Na, an alkaline earth metal cation such as Mg or Ca, another non-toxic metal cation such as Al or Zn or a non-toxic metalloid cation such as $NH_4^+$, piperazinium, 2-hydroxyethylammonium and the like.

In the above formula, alk is defined as ($C_1$–$C_3$) alkyl and includes methyl, ethyl, n-propyl or isopropyl.

The process of this invention comprises the administration of an effective amount of a drug according to the above formula preferably by the oral route, to a mammal having high urate blood concentrations and in need of treatment, said drug being mixed with a pharmaceutically acceptable excipient or diluent and administered in divided dosage form. Each dosage unit should contain from 2 to 20 mg./kg. of mammalian body weight of a drug of the above formula. We prefer to administer drugs according to the above formula in which R is OH or OM. Such drugs can be administered not only orally but also parenterally.

However, drugs in which R is other than OH or OM are not active parenterally. For parenteral administration, the drug is usually compounded in unit dosage form as a sodium or potassium salt in an isotonic solution. Such isotonic solutions are particularly adapted for iv or intraperitoneal injection. Parenteral intramuscular injection may be employed either using the free acid or a non-toxic, non-irritating salt thereof plus one or more of the usual pharmaceutical excipients used with intramuscular injections.

We prefer, however, to administer a drug according to the above formula by the oral route in carrying out the novel process of this invention. For such purpose, either a solid free acid or a non-toxic metal or metalloid salt can be employed. In addition, we have discovered that compounds according to the above formula in which R is other than OH or OM—those compounds which R is O-alk, NH2, NHalk or N(alk)2—can be employed as precursors of the free acid since such acid derivatives are hydrolyzed to the free acid at stomach pH. However, such hydrolysis is apparently not complete and the esters and amides of the isothiazolecarboxylic acids represented by formula I above are not as active anti-gout drugs on a weight for weight basis as are the free acids or the non-toxic anionic salts thereof. For oral administration, the free acid or an anionic salt thereof in solid form can be mixed with starch or other pharmaceutical excipient and the mixture loaded into telescoping gelatin capsules such that each capsule contains a dosage unit of from 100 to 500 mg. of a compound according to the above formula. Alternatively, starch, a binder, various lubricants, etc. can be mixed together and the mixture compressed into tablets such that each tablet contains a unit dosage having from 100 to 250 or even 500 mg. of the compound of the above formula. Such tablets can be scored so that half and quarter doses can be administered if desired.

Compounds useful in novel processes of this invention in the form of their free acid or salt thereof include the following:

3-(2-thienyl)-4-amino-5-isothiazolecarboxylic acid, sodium salt
3-(4-fluorophenyl)-4-chloro-5-isothiazolecarboxylic acid
3-(3-chlorophenyl)-5-isothiazolecarboxylic acid, calcium salt
3-(4-tolyl)-4-methylamino-5-isothiazolecarboxylic acid, ammonium salt
3-(3-ethylphenyl)-4-hydroxy-5-isothiazolecarboxylic acid, potassium salt
3-(3-pyridyl)-4-chloro-5-isothiazolecarboxylic acid, magnesium salt
3-(3-thienyl)-4-fluoro-5-isothiazolecarboxylic acid, tetramethylammonium salt
3-(3-anisyl)-4-bromo-5-isothiazolecarboxylic acid
3-(3,4-dimethoxyphenyl)-4-chloro-5-isothiazolecarboxylic acid, aluminum salt
3-(3,5-dimethoxyphenyl)-4-amino-5-isothiazolecarboxylic acid, calcium salt
3-(3-chloro-4-methylphenyl)-5-isothiazolecarboxylic acid, magnesium salt
3-(3,4-difluorophenyl)-4-amino-5-isothiazolecarboxylic acid
3-(4-trifluoromethyl-3-fluorophenyl)-4-hydroxy-5-isothiazolecarboxylic acid
3-(3,4-methylenedioxyphenyl)-4-hydroxy-5-isothiazolecarboxylic acid
3-(4-ethylphenyl)-4-amino-5-isothiazolecarboxylic acid, tetraethylammonium salt
3-(4-trifluoromethylphenyl)-5-isothiazolecarboxylic acid and the like.

A preferred group of compounds coming within the scope of the above formula, which compounds are unexpectedly active as xanthine oxidase inhibitors, are those in which Ar is 3-trifluoromethylphenyl. Illustrative of this preferred group of compounds are the following:

3-(3-trifluoromethylphenyl)-5-isothiazolecarboxylic acid
3-(3-trifluoromethylphenyl)-4-fluoro-5-isothiazolecarboxylic acid, sodium salt
3-(3-trifluoromethylphenyl)-4-chloro-5-isothiazolecarboxylic acid, ammonium salt
3-(3-trifluoromethylphenyl)-4-iodo-5-isothiazolecarboxylic acid, potassium salt
3-(3-trifluoromethylphenyl)-4-amino-5-isothiazolecarboxylic acid, calcium salt
3-(3-trifluoromethyl-4-fluorophenyl)-4-fluoro-5-isothiazolecarboxylic acid
3-(3-trifluoromethylphenyl)-4-hydroxy-5-isothiazolecarboxylic acid, magnesium salt
3-(3-trifluoromethyl-4-methoxyphenyl)-4-hydroxy-5-isothiazolecarboxylic acid, zinc salt; and the like.

Precursor compounds, those esters and amides according to I above which are transformed in the stomach after oral administration to carboxylic acids, include the following;

methyl 3-(3-trifluoromethylphenyl)-5-isothiazolecarboxylate
N,N-dimethyl-3-(4-chlorophenyl)-4-hydroxy-5-isothiazolecarboxamide
ethyl 3-(4-trifluoromethylphenyl)-4-amino-5-isothiazolecarboxylate
N-ethyl-3-(4-iodophenyl)-4-chloro-5-isothiazolecarboxamide
3-(3,5-xylyl)-4-bromo-5-isothiazolecarboxamide
3-(3,4-dimethoxy)-4-fluoro-5-isothiazolecarboxamide It will be apparent that other carboxylic acid derivatives in addition to esters, amides or lower alkylamides, can serve as precursors for the corresponding isothiazolecarboxylic acid upon oral administration; i.e., these carboxylic acid derivatives can be converted by the acid of the stomach (pH≅2) to the free carboxylic acid.

It will also be apparent to those skilled in the art that, upon oral administration of an isothiazole carboxylic acid, salt or precursor ester or precursor amide, the greater percentage of the isothiazole carboxylic acid will exist in the stomach in the unionized form; that is to say, the strong acid of the stomach, HCl at pH≅2 will suppress the ionization of the weaker acid according to the formula $$Ks = \frac{[H^+] \text{ [isothiazolecarboxylate ion]}}{\text{[isothiazolecarboxylic acid]}}$$

where Ks is the apparent dissociation constant for the particular isothiazolecarboxylic acid.

The compounds of this invention are prepared according to one or more of the following procedures. The preparation of compounds in which X is NH2 is illustrated in Procedure A.

PROCEDURE A

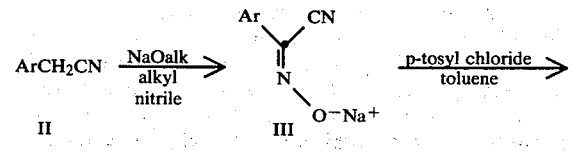

-continued
PROCEDURE A

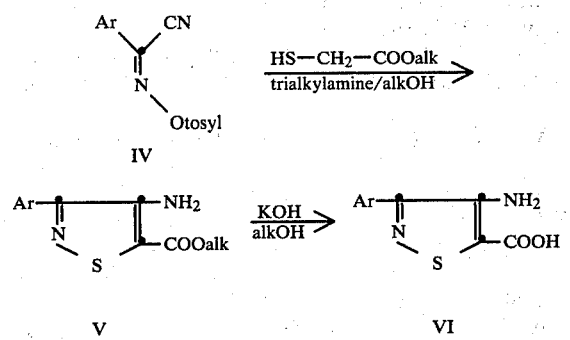

wherein Ar and alk have the same significance as before.

According to Procedure A, an arylacetonitrile, for example a substituted benzylcyanide (II), is reacted with a sodium alkanolate (NaOalk) to form a sodium salt and this salt is in turn reacted with an alkyl nitrite to yield an oximino derivative (III). Reaction of the sodium salt with p-toluenesulfonyl chloride (p-tosyl chloride) produces the corresponding tosyl ester (IV). Reaction of this oximinotosylate with a lower alkyl ester of thioglycolic acid in the presence of a tertiary alkyl amine or morpholine yields a lower alkyl 3-aryl-4-amino-5-isothiazolecarboxylate (V), which ester can be hydrolyzed with base in lower alkanol solution to yield the corresponding carboxylic acid (VI).

The preparation of 4-hydroxyisothiazolecarboxylic acids, compounds according to I in which X is OH, is illustrated according to Procedure B below.

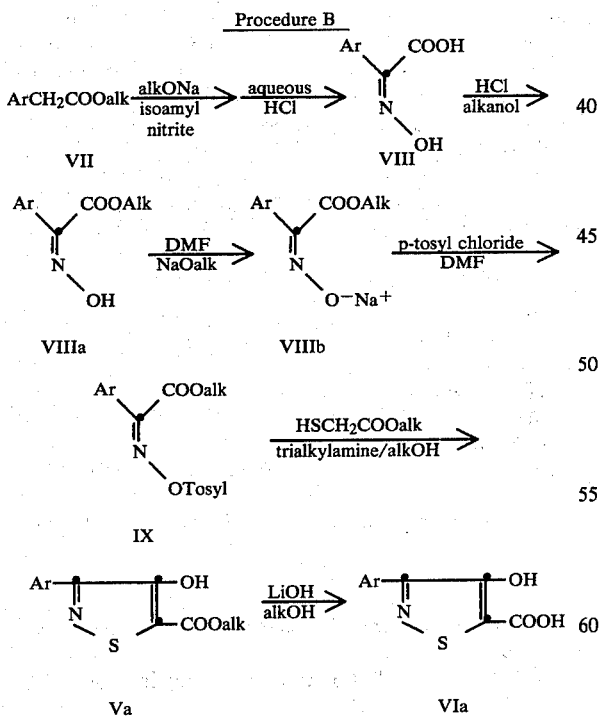

According to Procedure B, an arylacetic ester (VII) is reacted with a sodium alkanolate and the resulting sodium salt reacted with isoamyl nitrite followed by treatment with aqueous HCl to yield the aryloximino acid (VIII). Reesterification with an alkanol in the presence of acid such as HCl yields the aryloximino ester (VIIIa). Reaction of this ester with a sodium alkanolate in DMF produces the sodium salt of the oxime group (VIIIb). Reaction of the sodium salt with p-tosyl chloride, also in DMF, yields the corresponding p-toluenesulfiminoarylacetic ester (IX). Treatment of this ester with a lower alkyl ester of thioglycolic acid in the presence of triethylamine or other tertiary alkylamine or morpholine and a lower alkanol yields a lower alkyl 3-aryl-4-hydroxy-5-isothiazolecarboxylate ($V_a$) which, upon hydrolysis with base, yields the corresponding carboxylic acid ($VI_a$).

A non-aqueous diazotization reaction can be employed to prepare compounds according to formula I in which X is H. In this procedure, a 4-amino derivative prepared by Procedure A above, is reacted with isoamyl nitrite in THF solution. This procedure yields a diazonium species which decomposes to yield a compound with a hydrogen at C-4. It is preferred that this latter procedure be carried out on isothiazolecarboxylate esters (V) rather than on acids (VI).

Compounds according to formula I above in which X is hal—as for example, chloride, bromide, iodide or fluoride—are also prepared by a non-aqueous diazotization reaction using the 4-amino compound as a starting material. For instance, the diazonium species produced by the action of nitrosyl chloride on a 4-amino derivative is decomposed by heating to yield the corresponding 4-chloro derivative. Here again, it is preferred to use esters (V) as starting materials rather than free acids (VI). The free acids are, as before, readily prepared by hydrolysis of the 4-halo ester.

Compounds according to formula I above in which X is a lower alkylamino group or a lower alkyloxy group are prepared by reacting the sodium salt of the 4-amino-5-isothiazolecarboxylate ester (V) or of 4-hydroxy-5-isothiazolecarboxylate ester (Va) with methyl or ethyl iodide.

In order to prepare the 4-bromo derivatives or the 4-iodo derivatives of the 3-aryl-5-isothiazolecarboxylic acids, a mixture of isoamyl nitrite and bromine or iodine is used in place of the nitrosyl chloride used in preparing the 4-chloro compounds. The 4-fluoro derivatives are prepared by reacting the corresponding 4-amino ester (V) with nitrosonium tetrafluoroborate to form a salt followed by thermolysis of the salt thus obtained.

In a still further variation of the above procedures, 4-hydroxy derivatives can be prepared by reacting an arylglyoxylic acid with hydroxylamine hydrochloride to form the corresponding oxime. As before, the oxime is converted to the p-tosyl oxime ester which is then condensed with a thioglycolate ester to yield the desired 4-hydroxy-5-isothiazolecarboxylic acid ester directly.

This invention is further illustrated by the following specific examples.

EXAMPLE 1

Methyl 3-(4-methoxyphenyl)-4-amino-5-isothiazolecarboxylate

To a stirred solution of 8.25 g. of 4-methoxy-α-(para-toluenesulfonyloxyimino)benzylcyanide in 80 ml. of methanol containing 3.3 g. of methyl thioglycolate was added dropwise over a thirty minute period 5.0 g. of triethylamine. The reaction mixture was stirred at room temperature for four hours following complete addition, and then was cooled to 0° C. and filtered. The precipitate which was collected was recrystallized from hexane and ethyl acetate to provide 2.7 g. of methyl 3-(4-methoxyphenyl)-4-amino-5-isothiazolecarboxylate. Yield 42%. M.P. 129°–131° C.

Analysis calculated for $C_{12}H_{12}N_2O_3S$. Theory: C, 54.53; H, 4.58; N, 10.60. Found: C, 54.38; H, 4.48; N, 10.45.

The following additional 3-aryl-4-amino-5-isothiazolecarboxylic acid esters were prepared according to the general procedure set out in the above example by reacting the appropriate benzylcyanide oxime tosylate with an alkylthioglycolate.

Methyl 3-(3-methoxyphenyl)-4-amino-5-isothiazolecarboxylate. Yield 11%. M.P. 94°–95° C.

Analysis calculated for $C_{12}H_{12}N_2O_3S$. Theory: C, 54.53; H, 4.58; N, 10.60. Found: C, 54.73; H, 4.93; N, 10.69.

Methyl 3-(3-fluorophenyl)-4-amino-5-isothiazolecarboxylate. Yield 9%. M.P. 133°–134° C.

Analysis calculated for $C_{11}H_9FN_2O_2S$. Theory: C, 52.37; H, 3.60; N, 11.10. Found: C, 52.55; H, 3.72; N, 11.39.

Methyl 3-(4-fluorophenyl)-4-amino-5-isothiazolecarboxylate. M.P. 163° C.

Methyl 3-phenyl-4-amino-5-isothiazolecarboxylate. M.P. 114°–115° C.

Analysis calculated for $C_{11}H_{10}N_2O_2S$. Theory: C, 56.40; H, 4.30; N, 11.96. Found: C, 56.64; H, 4.10; N, 11.72.

Methyl 3-(4-chlorophenyl)-4-amino-5-isothiazolecarboxylate. M.P. 157°–158° C.

Analysis calculated for $C_{11}H_9ClN_2O_2S$. Theory: C, 49.17; H, 3.38; N, 10.42. Found: C, 49.45; H, 3.54; N, 10.65.

Methyl 3-(4-bromophenyl)-4-amino-5-isothiazolecarboxylate. M.P. 163°–165° C.

Analysis calculated for $C_{11}H_9BrN_2O_2S$. Theory: C, 42.19; H, 2.90; N, 8.95. Found: C, 42.25; H, 2.83; N, 8.98.

Methyl 3-(3-fluoro-4-methoxyphenyl)-4-amino-5-isothiazolecarboxylate. M.P. 182°–184° C.

Analysis calculated for $C_{12}H_{11}FN_2O_3S$. Theory: C, 51.06; H, 3.93; N, 9.92. Found: C, 51.23; H, 3.80; N, 9.88.

Methyl 3-(3,5-dimethoxyphenyl)-4-amino-5-isothiazolecarboxylate.

Methyl 3-(3,4-dichlorophenyl)-4-amino-5-isothiazolecarboxylate. M.P. 183°–184° C.

Analysis calculated for $C_{11}H_8Cl_2N_2O_2S$. Theory: C, 43.58; H, 2.66; N, 9.24. Found: C, 43.79; H, 2.49; N, 9.06.

Methyl 3-(4-methoxy-3-methylphenyl)-4-amino-5-isothiazolecarboxylate. M.P. 135°–137° C.

Analysis calculated for $C_{13}H_{14}N_2O_3S$. Theory: C, 56.10; H, 5.07; N, 10.07. Found: C, 56.10; H, 4.91; N, 9.80.

Methyl 3-(3,4-dimethoxyphenyl)-4-amino-5-isothiazolecarboxylate. M.P. 149°–151° C.

Analysis calculated for $C_{13}H_{14}N_2O_4S$. Theory: C, 53.05; H, 4.79; N, 9.52. Found: C, 53.29; H, 4.65; N, 9.27.

Methyl 3-(1,3-benzodioxyl-5-yl)-4-amino-5-isothiazolecarboxylate. M.P. 135°–137° C.

Analysis calculated for $C_{12}H_{10}N_2O_4S$. Theory: C, 51.79; H, 3.62; N, 10.07. Found: C, 52.02; H, 3.73; N, 10.03.

Methyl 3-(3-trifluoromethylphenyl)-4-amino-5-isothiazolecarboxylate. M.P. 94°–95° C.

Analysis calculated for $C_{12}H_9F_3N_2O_2S$. Theory: C, 47.68; H, 3.00; N, 9.27. Found: C, 47.93; H, 2.85; N, 9.50.

Methyl 3-(4-ethoxyphenyl)-4-amino-5-isothiazolecarboxylate.

Methyl 3-(3-chlorophenyl)-4-amino-5-isothiazolecarboxylate. M.P. 162°–164° C.

Analysis calculated for $C_{11}H_9ClN_2O_2S$. Theory: C, 49.17; H, 3.38; N, 10.42. Found: C, 49.39; H, 3.30; N, 10.56.

Methyl 3-(3-tolyl)-4-amino-5-thiothiazolecarboxylate. M.P. 114°–115° C.

Analysis calculated for $C_{12}H_{12}N_2O_2S$. Theory: C, 58.05; H, 4.87; H, 11.28. Found: C, 57.84; H, 4.83; N, 11.08.

Methyl 3-(4-trifluoromethylphenyl)-4-amino-5-isothiazolecarboxylate. M.P. 130°–131° C.

Analysis calculated for $C_{12}H_9F_3N_2O_2S$. Theory: C, 47.68; H, 3.00; N, 9.27. Found: C, 47.80; H, 3.08; N, 9.33.

Methyl 3-(4-propoxyphenyl)-4-amino-5-isothiazolecarboxylate.

Methyl 3-(4-isopropoxyphenyl)-4-amino-5-isothiazolecarboxylate. M.P. 125°–127° C.

Analysis calculated for $C_{14}H_{16}N_2O_3S$. Theory: C, 51.52; H, 5.52; N, 9.58. Found: C, 51.31; H, 5.27; N, 9.38.

Methyl 3-(p-tolyl)-4-amino-5-isothiazolecarboxylate. M.P. 151°–153° C.

Analysis calculated for $C_{12}H_{12}N_2O_2S$. Theory: C, 58.05; H, 4.87; N, 11.28. Found: C, 58.06; H, 5.05; N, 11.16.

EXAMPLE 2

Preparation of Carboxylic Acids

A solution of 2.0 g. of methyl 3-(4-methoxyphenyl)-4-amino-5-isothiazolecarboxylate and 0.5 g. of potassium hydroxide in 70 ml. of methanol was heated at reflux for six hours. The reaction mixture was then poured into 100 g. of ice containing 5 ml. of 12 N aqueous hydrochloric acid. The free acid precipitated from the acidic solution, and after all of the ice had melted, the aqueous acidic mixture was filtered. The precipitate was crystallized from ethanol and water to provide 1.3 g. of 4-amino-3-(4-methoxyphenyl)-5-isothiazolecarboxylic acid. Yield 65%. M.P. 215°–217° C.

Analysis calculated for $C_{11}H_{10}N_2O_3S$. Theory: C, 52.79; H, 4.03; N, 11.19. Found: C, 53.01; H, 4.27; N, 11.48.

NMR (DMSO):
3.8 (s) 3H, $CH_3$;
7.0–7.8 (dd) 4H, aromatic
6.0–8.0 (broad singlet) 3H, amine and acid protons.

The following additional 3-aryl-4-amino-5-isothiazolecarboxylic acids were prepared following the above general procedure by hydrolyzing the corresponding 4-amino-3-aryl-5-isothiazolecarboxylic acid ester.

3-(3-methoxyphenyl)-4-amino-5-isothiazolecarboxylic acid. M.P. 195°–198° C.

NMR (DMSO):
3.8 (s) 3H, $CH_3$;
6.8–8.0 (multiplet) 7H, aromatic, amine, and acid protons.

3-(3-fluorophenyl)-4-amino-5-isothiazolecarboxylic acid. M.P. 218°–219° C.

Analysis calculated for $C_{10}H_7FN_2O_2S$. Theory: C, 50.42; H, 2.96; N, 11.76. Found: C, 50.64; H, 3.20; N, 12.03.

NMR (DMSO):
7.2–7.7 (broad multiplet) 4H, aromatic 3-(4-fluorophenyl)-4-amino-5-isothiazolecarboxylic acid. M.P. 244° C. dec.

Analysis calculated for $C_{10}H_7FN_2O_2S$. Theory: C, 50.42; H, 2.96; N, 11.76. Found: C, 50.56; H, 3.10; N, 11.84.

3-phenyl-4-amino-5-isothiazolecarboxylic acid. M.P. 218°–220° C.

Analysis calculated for $C_{10}H_8N_2O_2S$. Theory: C, 54.53; H, 3.66; N, 12.72. Found: C, 54.73; H, 3.45; N, 12.98.

NMR (DMSO):
7.0–7.5 (broad singlet) 3H, amine, and acid protons
7.4–7.98 (multiplet) 5H, aromatic 3-(4-chlorophenyl)-4-amino-5-isothiazolecarboxylic acid. M.P. 218°–220° C.

Analysis calculated for $C_{10}H_7ClN_2O_2S$. Theory: C, 47.16; H, 2.77; N, 11.00. Found: C, 47.40; H, 2.96; N, 11.11.

3-(4-bromophenyl)-4-amino-5-isothiazolecarboxylic acid. M.P. 219°–220° C.

Analysis calculated for $C_{10}H_7BrN_2O_2S$. Theory: C, 40.15; H, 2.36; N, 9.36. Found: C, 40.07; H, 2.35; N, 9.37.

3-(3-fluoro-4-methoxyphenyl)-4-amino-5-isothiazolecarboxylic acid. Yield 37%. M.P. 213°–214° C.

Analysis calculated for $C_{11}H_9FN_2O_3S$. Theory: C, 49.25; H, 3.38; N, 10.44. Found: C, 49.36; H, 3.35; N, 10.40.

3-(3,5-dimethoxyphenyl)-4-amino-5-isothiazolecarboxylic acid. M.P. 198°–199° C.

Analysis calculated for $C_{12}H_{12}N_2O_4S$. Theory: C, 51.42; H, 4.32; N, 9.99. Found: C, 51.57; H, 4.42; N, 9.82.

3-(3,4-dichlorophenyl)-4-amino-5-isothiazolecarboxylic acid. Yield 80%. M.P. 249°–251° C.

Analysis calculated for $C_{10}H_6Cl_2N_2O_2S$. Theory: C, 41.54; H, 2.09; N, 9.69. Found: C, 41.78; H, 1.99; N, 9.64.

3-(4-methoxy-3-methylphenyl)-4-amino-5-isothiazolecarboxylic acid. Yield 18%. M.P. 206°–207° C.

Analysis calculated for $C_{12}H_{12}N_2O_3S$. Theory: C, 54.53; H, 4.58; N, 10.60. Found: C, 54.80; H, 4.74; N, 10.42.

3-(3,4-dimethoxyphenyl)-4-amino-5-isothiazolecarboxylic acid. Yield 94%. M.P. 200°–202° C.

Analysis calculated for $C_{12}H_{12}N_2O_4S$. Theory: C, 51.42; H, 4.32; N, 9.99. Found: C, 51.61; H, 4.24; N, 9.91.

3-(1,3-benzodioxyl-5-yl)-4-amino-5-isothiazolecarboxylic acid. Yield 32%. M.P. 218°–219° C.

Analysis calculated for $C_{11}H_8N_2O_4S$. Theory: C, 50.00; H, 3.05; N, 10.60. Found: C, 50.20; H, 3.10; N, 10.45.

3-(3-trifluoromethylphenyl)-4-amino-5-isothiazolecarboxylic acid. Yield 80%. M.P. 179°–180° C.

Analysis calculated for $C_{11}H_7F_3N_2O_2S$. Theory: C, 45.84; H, 2.45; N, 9.72. Found: C, 45.90; H, 2.46; N, 9.66.

3-(4-ethoxyphenyl)-4-amino-5-isothiazolecarboxylic acid. M.P. 195°–198° C.

Analysis calculated for $C_{12}H_{12}N_2O_3S$. Theory: C, 54.53; H, 4.58; N, 10.60. Found: C, 54.56; H, 4.52; N, 10.73.

3-(3-chlorophenyl)-4-amino-5-isothiazolecarboxylic acid. M.P. 222°–224° C.

Analysis calculated for $C_{10}H_7ClN_2O_2S$. Theory: C, 47.16; H, 2.77; N, 11.00. Found: C, 47.37; H, 2.87; N, 10.98.

3-(3-tolyl)-4-amino-5-isothiazolecarboxylic acid. M.P. 192°–193° C.

Analysis calculated for $C_{11}H_{10}N_2O_2S$. Theory: C, 56.40; H, 4.30; N, 11.96. Found: C, 56.53; H, 4.57; N, 11.97.

3-(4-trifluoromethylphenyl)-4-amino-5-isothiazolecarboxylic acid. Yield 94%. M.P. 210°–213° C.

Analysis calculated for $C_{11}H_7F_3N_2O_2S$. Theory: C, 45.84; H, 2.45; N, 9.72. Found: C, 45.84; H, 2.56; N, 9.71.

3-(p-tolyl)-4-amino-5-isothiazolecarboxylic acid. Yield 81%. M.P. 239° C. dec.

Analysis calculated for $C_{11}H_{10}N_2O_2S$. Theory: C, 56.40; H, 4.30; N, 11.96. Found: C, 56.27; H, 4.31; N, 12.23.

3-(4-propoxyphenyl)-4-amino-5-isothiazolecarboxylic acid. M.P. 199°–201° C. with dec. Yield 60%.

Analysis calculated for $C_{13}H_{14}N_2O_3S$. Theory: C, 56.10; H, 5.07; N, 10.07. Found: C, 56.27; H, 4.87; N, 9.97.

3-(4-isopropoxyphenyl)-4-amino-5-isothiazolecarboxylic acid. M.P. 197°–199° C. Yield 89.4%.

Analysis calculated for $C_{13}H_{14}N_2O_3S$. Theory: C, 56.12; H, 5.04; N, 10.07. Found: C, 56.07; H, 4.92; N, 10.13.

EXAMPLE 3

Preparation of methyl 3-(3-trifluoromethylphenyl)-5-isothiazolecarboxylate

A solution of 4.5 g. of methyl 3-(3-trifluoromethylphenyl)-4-amino-5-isothiazolecarboxylate and 5.1 g. of isoamyl nitrite in 50 ml. of tetrahydrofuran was heated to reflux for one-half hour. The reaction mixture then was cooled, and the solvent was removed by evaporation under reduced pressure to provide a solid product which was crystallized from ethanol and water to give 2.8 g. (66% yield) of methyl 3-(3-trifluoromethylphenyl)-5-isothiazolecarboxylate. M.P. 82°–83° C.

The following 3-aryl-5-isothiazolecarboxylic acid esters were prepared by reaction of isoamyl nitrite with the corresponding 3-aryl-4-amino-5-isothiazolecarboxylic acid ester according to the above procedure.

Methyl 3-(4-anisyl)-5-isothiazolecarboxylate. Yield 62%. M.P. 104°–105° C.

Analysis calculated for $C_{12}H_{11}NO_3S$. Theory: C, 57.82; H, 4.45; N, 5.62. Found: C, 57.54; H, 4.45; N, 5.84.

Methyl 3-(3-chlorophenyl)-5-isothiazolecarboxylate. Yield 64%. M.P. 106°–107° C.

Analysis calculated for $C_{11}H_8ClNO_2S$. Theory: C, 52.08; H, 3.18; N, 5.52. Found: C, 52.03; H, 2.96; N, 5.49.

Methyl 3-(4-chlorophenyl)-5-isothiazolecarboxylate. Yield 47%. M.P. 112°–113° C.

Analysis calculated for $C_{11}H_8ClNO_2S$. Theory: C, 52.08; H, 3.18; N, 5.52. Found: C, 52.26; H, 3.20; N, 5.67.

Methyl 3-(3-anisyl)-5-isothiazolecarboxylate. Yield 73%. M.P. 95°–96° C.

Analysis calculated for $C_{12}H_{11}NO_3S$. Theory: C, 57.82; H, 4.45; N, 5.62. Found: C, 57.99; H, 4.43; N, 5.66.

EXAMPLE 4

Preparation of 3-(3-trifluoromethylphenyl)-5-isothiazolecarboxylic acid

A solution of 1.6 g. of methyl 3-(3-trifluoromethylphenyl)-5-isothiazolecarboxylate in 30 ml. of 95% alcohol containing 1.0 g. of potassium hydroxide was heated at reflux for one hour. The reaction mixture then was added to 50 g. of ice, and the aqueous solution was acidified by the addition of 12 N aqueous hydrochloric acid. The product which precipitated was collected by filtration and crystallized from toluene and hexane to provide 1.3 g. of 3-(3-trifluoromethylphenyl)-5-isothiazolecarboxylate acid. Yield 85%. M.P. 162.5°–164° C.

Analysis calculated for $C_{11}H_6F_3NO_2S$. Theory: C, 48.35; H, 2.21; N, 5.13; S, 11.74. Found: C, 48.57; H, 2.39; N, 5.31; S, 11.84.

By following the above procedure, the following 3-aryl-5-isothiazolecarboxylic acids were prepared by hydrolysis of the corresponding methyl esters.

3-(4-anisyl)-5-isothiazolecarboxylic acid. Yield 90%. M.P. 191°–192° C.

Analysis calculated for $C_{11}H_9NO_3S$. Theory: C, 56.16; H, 3.86; N, 5.95. Found: C, 56.04; H, 3.80; N, 6.16.

3-(3-chlorophenyl)-5-isothiazolecarboxylic acid. Yield 85%. M.P. 176°–177° C.

Analysis calculated for $C_{10}H_6ClNO_2S$. Theory: C, 50.11; H, 2.52; N, 5.84. Found: C, 49.86; H, 2.35; N, 5.64.

3-(4-chlorophenyl)-5-isothiazolecarboxylic acid. Yield 85%. M.P. 209°–210° C.

Analysis calculated for $C_{10}H_6ClNO_2S$. Theory: C, 50.11; H, 2.52; N, 5.84. Found: C, 50.37; H, 2.71; N, 5.76.

3-(3-anisyl)-5-isothiazolecarboxylic acid. Yield 88%. M.P. 194°–195° C.

Analysis calculated for $C_{11}H_9NO_3S$. Theory: C, 56.16; H, 3.86; N, 5.95. Found: C, 56.37; H, 4.00; N, 5.89.

EXAMPLE 5

Preparation of 3-(3-trifluoromethylphenyl)-4-chloro-5-isothiazolecarboxylic acid Excess nitrosyl chloride was bubbled over a five minute period into a cold (0° C.) stirred solution of 10.0 g. of methyl 3-(3-trifluoromethylphenyl)-4-amino-5-isothiazolecarboxylate in 150 ml. of chloroform. The reaction mixture was heated on a steam bath for five minutes, and then cooled to room temperature. Five grams of silica gel were added to the reaction mixture to remove any moisture. The silica gel was then removed by filtration, and the solvent was removed from the filtrate by evaporation under reduced pressure to provide the product as a solid residue. The solid was crystallized from ethanol and water to give 6.75 g. of methyl 3-(3-trifluoromethylphenyl)-4-chloro-5-isothiazolecarboxylate. Yield 61%. M.P. 54°–55° C.

A solution of 2.5 g. of methyl 3-(3-trifluoromethylphenyl)-4-chloro-5-isothiazolecarboxylate in 30 ml. of 95% alcohol containing 2.0 g. of potassium hydroxide was heated at reflux for eighteen hours. The reaction mixture then was added to 50 g. of ice, and the pH was adjusted to 2.0 with 12 N aqueous hydrochloric acid. The resulting precipitate was filtered and recrystallized from toluene and hexane to afford 1.6 g. of 3-(3-trifluoromethylphenyl)-4-chloro-5-isothiazolecarboxylic acid. Yield 67%. M.P. 148°–149° C.

Analysis calculated for $C_{11}H_5ClF_3NO_2S$. Theory: C, 42.94; H, 1.64; N, 4.55. Found: C, 43.24; H, 1.48; N, 4.78.

By using the general procedure set forth in Example 5, nitrosyl chloride was reacted with the appropriate 3-aryl-4-amino-5-isothiazolecarboxylate ester to provide the corresponding 4-chloro derivative, which after basic hydrolysis, gave the following 4-chloro-3-aryl-5-isothiazolecarboxylic acids.

3-(4-anisyl)-4-chloro-5-isothiazolecarboxylic acid. Yield from the ester 75%. M.P. 207°–208° C.

Analysis calculated for $C_{11}H_8ClNO_3S$. Theory: C, 48.99; H, 2.99; N, 5.19. Found: C, 49.26; H, 3.08; N, 5.36.

3-(3-chlorophenyl)-4-chloro-5-isothiazolecarboxylic acid. Yield from the ester 87%. M.P. 182°–183° C.

Analysis calculated for $C_{10}H_5Cl_2NO_2S$. Theory: C, 43.82; H, 1.84; N, 5.11. Found: C, 43.98; H, 1.91; N, 5.35.

3-(3-anisyl)-4-chloro-5-isothiazolecarboxylic acid. Yield from the ester 74%. M.P. 173°–174° C.

Analysis calculated for $C_{11}H_8ClNO_3S$. Theory: C, 48.99; H, 2.99; N, 5.19. Found: C, 48.72; H, 3.12; N, 5.33.

3-(3-fluorophenyl)-4-chloro-5-isothiazolecarboxylic acid. Yield from the ester 73%. M.P. 187°–188° C.

Analysis calculated for $C_{10}H_5ClFNO_2S$. Theory: C, 46.61; H, 1.96; N, 5.44. Found: C, 46.33; H, 2.05; N, 5.48.

3-(3-tolyl)-4-chloro-5-isothiazolecarboxylic acid. Yield from the ester 84%. M.P. 161°–162° C.

Analysis calculated for $C_{11}H_8ClNO_2S$. Theory: C, 52.08; H, 3.18; N, 5.52. Found: C, 52.07; H, 3.20; N, 5.70.

3-(4-fluorophenyl)-4-chloro-5-isothiazolecarboxylic acid. Yield from the ester 74%. M.P. 202°–203° C.

Analysis calculated for $C_{10}H_5ClFNO_2S$. Theory: C, 46.61; H, 1.96; N, 5.44. Found: C, 46.82; H, 1.72; N, 5.30.

3-phenyl-4-chloro-5-isothiazolecarboxylic acid. Yield from the ester 50%. M.P. 184°–185° C.

Analysis calculated for $C_{10}H_6ClNO_2S$. Theory: C, 50.11; H, 2.52; N, 5.84. Found: C, 49.87; H, 2.37; N, 5.62.

3-(4-tolyl)-4-chloro-5-isothiazolecarboxylic acid. Yield from the ester 92%. M.P. 191°–192° C.

Analysis calculated for $C_{11}H_8ClNO_2S$. Theory: C, 52.08; H, 3.18; N, 5.52. Found: C, 51.82; H, 3.02; N, 5.79.

3-(4-chlorophenyl)-4-chloro-5-isothiazolecarboxylic acid. Yield from the ester 70%. M.P. 203°–204° C.

Analysis calculated for $C_{10}H_5Cl_2NO_2S$. Theory: C, 43.82; H, 1.84; N, 5.11. Found: C, 43.94; H, 1.96; N, 5.21.

EXAMPLE 6

Preparation of 3-(3-trifluoromethylphenyl)-4-bromo-5-isothiazolecarboxylic acid

To a stirred solution of 4.5 g. of methyl 3-(3-trifluorophenyl)-4-amino-5-isothiazolecarboxylate in 50 ml. of chloroform containing 5 ml. of bromine were added 2.6 g. of isoamyl nitrite. The reaction mixture was heated to reflux for ten minutes, after which time the solvent was removed by evaporation under reduced pressure to provide the product as a crude oil. The oil was purified by chromatography over 100 g. of silica gel, eluting with toluene. The fractions shown by thin layer chromatography to contain the desired product were combined and the solvent was removed therefrom by evaporation under reduced pressure to give a solid product. The solid thus formed was crystallized from ethanol to provide 2.2 g. of methyl 3-(3-trifluoromethylphenyl)-4-bromo-5-isothiazolecarboxylate. Yield 53%. M.P. 53°–55° C.

Analysis calculated for $C_{12}H_7BrF_3NO_2S$. Theory: C, 39.36; H, 1.93; N, 3.83; Br, 21.86. Found: C, 39.12; H, 1.96; N, 3.96; Br, 22.06.

Following the above procedure, 5.0 g. of ethyl 3-phenyl-4-amino-5-isothiazolecarboxylate were treated with bromine and isoamyl nitrite to yield 3.7 g. of ethyl 3-phenyl-4-bromo-5-isothiazolecarboxylate. M.P. 72°–73° C. (from 95% ethanol)

Analysis calculated for $C_{12}H_{10}BrNO_2S$. Theory: C, 46.17; H, 3.23; N, 4.49. Found: C, 46.14; H, 3.02; N, 4.44.

A solution of 2.0 g. of methyl 3-(3-trifluoromethylphenyl)-4-bromo-5-isothiazolecarboxylate and 1.0 g. of potassium hydroxide in 35 ml. of 95% alcohol was heated at reflux for one hour. The reaction mixture then was added to 50 g. of ice, and the aqueous mixture was acidified by the addition of 12 N aqueous hydrochloric acid. The solid which precipitated was collected by filtration and crystallized from toluene and hexane to provide 1.55 g. of 3-(3-trifluoromethylphenyl)-4-bromo-5-isothiazolecarboxylic acid. Yield 80%. M.P. 157°–158° C.

Analysis calculated for $C_{11}H_5BrF_3NO_2S$. Theory: C, 37.52; H, 1.43; N, 3.98; Br, 9.94. Found: C, 37.36; H, 1.47; N, 4.02; Br, 10.02.

The following 3-aryl-4-bromo-5-thiazolecarboxylic acids were prepared from the corresponding methyl 4-amino-3-aryl-5-thiazolecarboxylates according to the method of Example 6.

3-(3-chlorophenyl)-4-bromo-5-isothiazolecarboxylic acid. Yield from the corresponding methyl ester 70%. M.P. 190°–191° C.

Analysis calculated for $C_{10}H_5BrClNO_2S$. Theory: C, 37.70; H, 1.58; N, 4.40. Found: C, 37.95; H, 1.61; N, 4.59.

3-phenyl-4-bromo-5-isothiazolecarboxylic acid. Yield 0.8 g. (from 1.9 g. of ethyl ester) from toluene.

Analysis calculated for $C_{10}H_5BrNO_2S$. Theory: C, 42.27; H, 2.13; N, 4.93. Found: C, 42.11; H, 2.09; N, 4.65.

3-(4-chlorophenyl)-4-bromo-5-isothiazolecarboxylic acid. Yield from the corresponding methyl ester 50%. M.P. 206°–207° C.

Analysis calculated for $C_{10}H_5BrClNO_2S$. Theory: C, 37.70; H, 1.58; N, 4.40. Found: C, 38.01; H, 1.87; N, 4.67.

By following the general procedures set forth in Example 6, 3-aryl-4-amino-5-isothiazole carboxylic acid esters were reacted with isoamyl nitrite and iodine to give the corresponding 3-aryl-4-iodo-5-isothiazole carboxylic acid esters which, upon hydrolysis, afforded the following:

3-(3-trifluoromethylphenyl)-4-iodo-5-isothiazolecarboxylic acid. Yield from the corresponding methyl ester 67%. M.P. 177°–178° C.

Analysis calculated for $C_{11}H_5F_3INO_2S$. Theory: C, 33.10; H, 1.26; N, 3.51. Found: C, 33.29; H, 1.22; N, 3.56.

3-(3-chlorophenyl)-4-iodo-5-isothiazolecarboxylic acid. Yield from the corresponding methyl ester 63%. M.P. 195°–196° C.

Analysis calculated for $C_{10}H_5ClINO_2S$. Theory: C, 32.85; H, 1.38; N, 3.83. Found: C, 33.08; H, 1.25; N, 4.11.

3-(3-anisyl)-4-iodo-5-isothiazolecarboxylic acid. Yield from the corresponding methyl ester 35%. M.P. 176°–178° C.

Analysis calculated for $C_{11}H_8INO_3S$. Theory: C, 36.58; H, 2.23; N, 3.88. Found: C, 36.86; H, 2.17; N, 4.14.

3-(4-chlorophenyl)-4-iodo-5-isothiazolecarboxylic acid. Yield from the corresponding methyl ester 80%. M.P. 218°–219° C.

Analysis calculated for $C_{10}H_5ClINO_2S$. Theory: C, 32.85; H, 1.38; N, 3.83. Found: C, 33.10; H, 1.38; N, 3.89.

EXAMPLE 7

Preparation of 3-(3-trifluoromethylphenyl)-4-fluoro-5-isothiazolecarboxylic acid A solution of 4.5 g. of methyl 3-(3-trifluoromethylphenyl)-4-amino-5-isothiazolecarboxylate and 1.9 g. of nitrosonium tetrafluoroborate in 75 ml. of carbon tetrachloride was heated at reflux for one hour. The solvent was then removed by evaporation under reduced pressure to provide a solid residue. The solid was heated with an open flame until gaseous boron trifluoride and nitrogen were evolved. The solid then was cooled and the cooled solid dissolved in ethyl acetate. The organic solution was washed once with 2 N aqueous sodium hydroxide and once with brine, and was then dried. The solvent was removed by evaporation under reduced pressure. The resulting residue was chromatographed over 100 g. of silica gel, eluting with toluene. Fractions containing the desired product were combined and the solvent was evaporated therefrom to afford 900 mg. of methyl 3-(3-trifluoromethylphenyl)-4-fluoro-5-isothiazolecarboxylate. M.P. 78°–79° C.

The ester thus prepared was dissolved in 25 ml. of 95% alcohol containing 300 mg. of potassium hydroxide. The solution was heated at reflux for thirty minutes, and then poured into 50 g. of ice and acidified by the addition of 12 N aqueous hydrochloric acid. The acidic solution was extracted several times with ethyl acetate. The extracts were combined, washed with water, dried, and the solvent was removed by evaporation under reduced pressure to provide the product as a solid. The solid was crystallized from toluene and petroleum ether to afford 270 mg. of 3-(3-trifluoromethylphenyl)-4-fluoro-5-isothiazolecarboxylic acid. Yield from the ester, 30%. M.P. 144°–145° C.

Analysis calculated for $C_{11}H_5F_4NO_2S$. Theory: C, 45.37; H, 1.73; N, 4.81. Found: C, 45.10; H, 1.82; N, 4.59.

EXAMPLE 8

Preparation of methyl 3-(3-trifluoromethylphenyl)-4-hydroxy-5-isothiazolecarboxylate To a cold (0°–5° C.) stirred solution of 28 g. of potassium methoxide in 400 ml. of methanol were added in one portion 88 g. of methyl 2-(3-trifluoromethylphenyl)acetate, followed by the addition in one portion of 48 g. of isoamyl nitrite. The reaction mixture was warmed to room temperature and was stirred for twelve hours. After cooling the reaction mixture to 0° C., an additional 14 g. of potassium methoxide was added in one portion, followed by the addition of an additional 24 g. of isoamyl nitrite. The reaction mixture was again warmed to room temperature, and was stirred for an additional seventy-two hours. Once again the reaction mixture was cooled to 0° C. and an additional 14 g. of potassium methoxide and 24 g. of isoamyl nitrite were added. The reaction mixture was then warmed to room temperature, and the solvent was removed by evaporation under reduced pressure. The residue was dissolved in 600 ml. of water, and the aqueous solution was stirred for twenty-four hours at ambient temperature. The product was then washed with diethyl ether, and the ether extracts discarded. The aqueous solution was cooled to 0° C. in an ice bath, and acidified by the addition of 12 N aqueous hydrochloric acid. The precipitate which formed was collected by filtration and dried to give 95 g. of 3-trifluoromethylbenzoylformic acid oxime. M.P. 152°–156° C.

Analysis calculated for $C_9H_6F_3NO_3$. Theory: C, 46.37; H, 2.59; N, 6.01. Found: C, 46.33; H, 2.61; N, 6.08.

A solution of 50 g. of 3-trifluoromethylbenzoylformic acid oxime in 600 ml. of methanol containing 14.9 g. of hydroxylamine hydrochloride was stirred while hydrogen chloride gas was bubbled through the solution. The reaction mixture then was heated at reflux for three hours. After cooling the reaction mixture to room temperature, hydrogen chloride gas was bubbled into the reaction mixture for an additional five minutes, after which time the reaction mixture was again heated to reflux for two hours. The reaction mixture was evaporated to dryness in vacuo and the resulting residue was cooled to 25° C. A mixture of 50 ml. of diethyl ether and 50 ml. of water was added. The ethereal layer was separated, washed three times with 50 ml. portions of water, dried, and the solvent was removed by evaporation under reduced pressure to provide a solid residue. The solid was crystallized from pentane to afford 36 g. of methyl 2-(3-trifluoromethylphenyl)-2-hydroxyiminoacetate.

A solution of 36 g. of methyl 2-(3-trifluoromethylphenyl)-2-hydroxyiminoacetate in 100 ml. of N,N-dimethylformamide containing 7.9 g. of sodium methoxide was stirred for several minutes. The methanol was removed under reduced pressure and the reaction mixture was then cooled to 0° C., whereupon 27.7 g. of para-toluenesulfonyl chloride was added portionwise over fifteen minutes. Following complete addition, the reaction mixture was added to 100 g. of ice, and after all of the ice had melted, the aqueous mixture was filtered to provide the product as a soft solid. The solid so formed was suspended in 100 ml. of 1:1 diethyl ether and pentane. The suspension was filtered to afford 6.4 g. of methyl 2-(3-trifluoromethylphenyl)-2-(p-toluenesulfonyloxy)iminoacetate. M.P. 100°–108° C.

To a stirred solution of 6.4 g. of methyl 2-(3-trifluoromethylphenyl)-2-(p-toluenesulfonyloxy)iminoacetate in 50 ml. of methanol were added in one portion 1.7 g. of methyl thioglycolate and 2.1 g. of diisopropylethylamine. The reaction mixture was heated at reflux for two hours. An additional 0.5 g. of methyl thioglycolate and 0.5 g. of diisopropylethylamine were added to the reaction mixture, and refluxing was continued for an additional one hour. An additional 0.5 g. of methyl thioglycolate and 0.5 g. of diisopropylethylamine were added to the reaction mixture, and the mixture was heated at reflux for another hour. The reaction mixture next was poured into 100 g. of ice, and the pH was adjusted to 2 by the addition of 12 N aqueous hydrochloric acid. The precipitate which formed was collected by filtration, and then dissolved in 50 ml. of ethyl acetate. The organic layer was dried and concentrated by evaporation of the solvent. The residual product was then chromatographed over silica gel, using a 1:2 mixture of ethyl acetate and hexane as eluant. The appropriate fractions were combined and the solvent was removed by evaporation under reduced pressure to provide a solid. The solid was crystallized from pentane and then recrystallized from pentane and ethyl acetate to provide 1.1 g. of methyl 3-(3-trifluoromethylphenyl)-4-hydroxy-5-isothiazolecarboxylate. M.P. 108°–109° C.

EXAMPLE 9

Preparation of 3-(3-trifluoromethylphenyl-4-hydroxy-5-isothiazolecarboxylic acid A solution of 2.1 g. of lithium hydroxide and 2.1 g. of methyl 3-(3-trifluoromethylphenyl)-4-hydroxy-5-isothiazolecarboxylate in 50 ml. of methanol was heated at reflux for twelve hours. Following the addition of 3.0 g. more of lithium hydroxide, the reaction mixture was heated at reflux for an additional four hours, and then added to 100 g. of ice. The aqueous mixture was washed with 50 ml. of dichloromethane, and then acidified to pH 2 by the addition of 12 N aqueous hydrochloric acid. The precipitate which formed was collected by filtration, washed with water and dried. The solid thus formed was crystallized from toluene to afford 1.2 g. of 3-(3-trifluoromethylphenyl)-4-hydroxy-5-isothiazolecarboxylic acid. M.P. 155°–159° C. (decomposition).

The above reaction was repeated with 250 mg. of methyl 3-(3-trifluoromethyphenyl)-4-hydroxy-5-isothiazolecarboxylate and 250 mg. of lithium hydroxide to give 210 mg. of 3-(3-trifluoromethylphenyl)-4-hydroxy-5-isothiazolecarboxylic acid. M.P. 179°–182° C. (decomposition).

Analysis calculated for $C_{11}H_6F_3NO_3S$. Theory: C, 45.67; H, 2.08; N, 4.84. Found: C, 45.62; H, 1.96; N, 4.97.

EXAMPLE 10

Preparation of methyl 3-phenyl-4-hydroxy-5-isothiazolecarboxylate

A solution of 15 g. of phenylglyoxylic acid and 7 g. of hydroxylamine hydrochloride in 50 ml. of methanol was heated at reflux for twelve hours. After cooling the reaction mixture to room temperature, the solvent was removed by evaporation under reduced pressure to provide a solid residue. The solid was crystallized from ethanol and water to give 6.6 g. of methyl phenylglyoxylate oxime. M.P. 138°–142° C.

Analysis calculated for $C_9H_9NO_3$. Theory: C, 60.33; H, 5.06; N, 7.82. Found: C, 60.59; H, 4.94; N, 8.06.

A solution of 3.6 g. of the oxime from above and 1.1 g. of sodium methoxide in 50 ml. of N,N-dimethylformamide was stirred at ambient temperature for fifteen minutes. The methanol was then removed by evaporation under reduced pressure. The reaction mixture was stirred, and 3.8 g. of para-toluenesulfonyl chloride was added portionwise over ten minutes. After being stirred for an additional sixty minutes, the reaction mixture was added to 50 ml. of ice water. The aqueous mixture was filtered and the collected precipitate was crystallized from ethanol to provide 1.3 g. of methyl 2-phenyl-toluenesulfonyloxyiminoacetate. M.P. 143°–144° C.

A solution of 7.6 g. of the oxime tosylate prepared as described above in 75 ml. of methanol containing 2.8 g. of methyl thioglycolate and 3.4 g. of diisopropylethylamine was heated at reflux for three hours and then stirred for twelve hours at room temperature. The reaction mixture was evaporated under reduced pressure and the residue added to a mixture of 50 ml. of diethyl ether and 50 ml. of water. The ethereal layer was separated, washed with fresh water, dried, and the solvent was removed by evaporation under reduced pressure to provide methyl 3-phenyl-4-hydroxy-5-isothiazolecarboxylate.

EXAMPLE 11

Preparation of 3-phenyl-4-hydroxy-5-isothiazolecarboxylic acid

A mixture of 5.5 g. of methyl 3-phenyl-4-hydroxy-5-isothiazolecarboxylate and 4.0 g. of 50% aqueous sodium hydroxide in 100 ml. of diethyl ether was stirred at 24° C. for two hours. The reaction mixture was next diluted with 20 ml. of water, and an additional 4.0 g. of 50% aqueous sodium hydroxide was added. The reaction mixture was heated at 100° C. for thirty minutes, and then added to a mixture of 50 ml. of water and 50 ml. of diethyl ether. The aqueous layer was separated, washed with fresh diethyl ether, and then acidified to pH 2 by the addition of 12 N aqueous hydrochloric acid. The resulting precipitate was separated by filtration, and the solid product thus obtained was crystallized from toluene and ethyl acetate to give 0.8 g. of 3-phenyl-4-hydroxy-5-isothiazolecarboxylic acid. M.P. 161°–163° C.

Analysis calculated for $C_{10}H_7NO_3S$. Theory: C, 54.29; H, 3.19; N, 6.33. Found: C, 54.01; H, 3.34; N, 6.48.

EXAMPLE 12

Preparation of 3-(3-trifluoromethylphenyl)-4-methylamino-5-isothiazolecarboxylic acid A suspension of 0.5 g. of sodium hydride (washed free of mineral oil) in 15 ml. of tetrahydrofuran was cooled to −20° C. and stirred. To the cold stirred suspension was added in one portion 3.0 g. of methyl 3-(3-trifluoromethylphenyl)-4-amino-5-isothiazolecarboxylate. The reaction mixture was warmed to room temperature, at which time 1.5 ml. of methyl iodide was added in one portion. The reaction mixture was stirred at ambient temperature for two hours, and then was added to 50 ml. of ice water. The aqueous mixture was extracted several times with diethyl ether. The ethereal extracts were combined, washed with water, dried and the solvent was removed by evaporation under reduced pressure to afford 2.0 g. of methyl 4-methylamino-3-(3-trifluoromethylphenyl)-5-isothiazolecarboxylate.

Hydrolysis of the methyl ester thus formed by reaction with 0.5 g. of potassium hydroxide afforded, after crystallization from hexane and ethyl acetate, 1.0 g. of 3-(3-trifluoromethylphenyl)-4-methylamino-5-isothiazolecarboxylic acid. M.P. 138°–141° C.

Analysis calculated for $C_{12}H_9F_3N_2O_2S$. Theory: C, 47.68; H, 3.00; N, 9.27. Found: C, 47.86; H, 3.07; N, 9.28.

EXAMPLE 13

Preparation of 3-(2-thienyl)-4-amino-5-isothiazolecarboxylic acid

To a stirred cold (−30° C.) solution of 20.2 g. of sodium methoxide in 100 ml. of ethanol was added in one portion a solution of 50.0 g. of 2-thiopheneacetonitrile and 39.8 g. of isoamyl nitrite in 75 ml. of ethanol. The reaction mixture was stored at 0° C. for six hours, and then diluted by the addition of 350 ml. of diethyl ether. The solid precipitate was collected by filtration and dried to give 22 g. of 2-thiopheneglyoxylonitrile oxime sodium salt.

A solution of 22 g. of the oxime sodium salt from above and 26.4 g. of p-toluenesulfonyl chloride in 250 ml. of benzene was heated at reflux for three hours. The reaction mixture was cooled to room temperature and diluted with 50 ml. of water and 100 ml. of ethyl acetate. The organic layer was separated, dried, and the solvent was removed by evaporation under reduced pressure to provide 11.5 g. of α-(p-toluenesulfonyloxyimino)-2-thiopheneacetonitrile. M.P. 113°–119° C.

A solution of 11.5 g. of the oxime tosylate in 200 ml. of methanol containing 5.0 g. of methylthioglycolate and 5.5 ml. of triethylamine was stirred at ambient temperature for sixteen hours. The reaction mixture was diluted with 100 ml. of water, and the product was extracted therefrom into ethyl acetate and hexane. The extracts were combined and the solvent was removed by evaporation under reduced pressure to provide a solid which, following purification by chromatography over silica gel, yielded 1.8 g. of purified methyl 3-(2-thienyl)-4-amino-5-isothiazolecarboxylate.

The methyl ester thus formed was hydrolyzed by reaction with sodium hydroxide in ethanol and water to provide 3-(2-thienyl)-4-amino-5-isothiazolecarboxylic acid. M.P. 221°–224° C.

Analysis calculated for $C_8H_6N_2O_2S_2$. Theory: C, 42.46; H, 2.67; N, 12.38; S, 28.34. Found: C, 42.18; H, 2.48; N, 12.13; S, 28.07.

EXAMPLE 14

Preparation of 3-(3-pyridyl)-4-amino-5-isothiazolecarboxylic acid

Following the procedure of Example 13, 25 g. of 3-pyridylacetonitrile were reacted with 11.6 g. of sodium methoxide and 25 g. of isoamyl nitrite to provide 15.7 g. of 3-pyridylglyoxylonitrile oxime, sodium salt. The oxime sodium salt thus formed was reacted with 20.0 g. of p-toluenesulfonyl chloride in benzene to provide, after crystallization from acetonitrile, 17.0 g. of α-(p-toluenesulfonyloxyimino)-3-pyridylacetonitrile. M.P. 158°–160° C.

Analysis calculated for $C_{14}H_{11}N_3O_3S$. Theory: C, 55.81; H, 3.68; N, 13.95. Found: C, 55.69; H, 3.53; N, 13.77.

To a stirred solution of 6.0 g. of methyl thioglycolate and 5.7 g. of triethylamine in 100 ml. of methanol was added in one portion 17.0 g. of α-(p-toluenesulfonyloxyimino)-3-pyridylacetonitrile. The reaction mixture was stirred at room temperature for sixteen hours, and then was added to 100 ml. of water. The aqueous mixture was extracted several times with chloroform. The organic extracts were combined, dried, and the solvent was removed by evaporation under reduced pressure to provide a solid residue. The solid was crystallized from ethanol to give 15 g. of methyl 3-(3-pyridyl)-4-amino-5-isothiazolecarboxylate. M.P. 177°–179° C.

Analysis calculated for $C_{10}H_9N_3O_2S$. Theory: C, 51.05; H, 3.86; N, 17.86. Found: C, 50.86; H, 3.81; N, 17.64.

A solution of 1.8 g. of methyl 3-(3-pyridyl)-4-amino-5-isothiazolecarboxylate in 20 ml. of ethanol and 20 ml. of water containing three pellets of sodium hydroxide was heated at reflux for ninety minutes. The reaction mixture was then added to 50 ml. of ice water, and the aqueous mixture was acidified by the addition of 1 N aqueous hydrochloric acid. The solid precipitate was collected by filtration and recrystallized from acetic acid and water to provide 3-(3-pyridyl)-4-amino-5-isothiazolecarboxylic acid. M.P. 235°–236° C.

Analysis calculated for $C_9H_7N_3O_2S$. Theory: C, 48.86; H, 3.19; N, 18.99. Found: C, 48.88; H, 3.38; N, 19.23.

Amides of the isothiazolecarboxylic acids of this invention (I above where R is $NH_2$ or NHalk) are prepared by treating the corresponding ester with $NH_3$, methylamine or ethylamine in a mutual inert solvent, preferably in a sealed tube or autoclave. A typical preparation of an amide follows.

EXAMPLE 15

Preparation of N-methyl 3-(3-trifluoromethylphenyl)-4-amino-5-iso-thiazolecarboxamide One hundred ml. of methanol were saturated with gaseous methyl amine. Two grams of ethyl 3-(3-trifluoromethylphenyl)-4-amino-5-isothiazolecarboxylate were added. The reaction mixture was stirred at ambient temperature for about 30 minutes and was then heated to refluxing temperature for about 30 minutes. TLC indicated some amide had formed. Gaseous methylamine was bubbled through the refluxing reaction mixture for about 4 additional hours, at which time TLC indicated starting material was no longer present. The reaction mixture was poured into an ice-water mixture. N-methyl 3-(3-trifluoromethylphenyl)-4-amino-5-isothiazolecarboxamide formed in the above reaction precipitated and the precipitate collected by filtration. M.P. 113° C. (after vacuum drying). Yield 1.4 g.

Analysis calculated for $C_{12}H_{10}F_3N_3O_5$. Theory: C, 47.94; H, 3.35; N, 30.95. Found: C, 48.09; H, 3.30; N, 30.72.

Alternatively, a reactive derivative, acid chloride, anhydride or mixed anhydride can be prepared from a 5-isothiazolecarboxylic acid according to Formula I and this reactive intermediate contacted with ammonia or an amine to yield the corresponding amide. However, where X in Formula I is an interfering group ($NH_2$, NHalk, or OH), a different procedure must be used because the reactive acid derivative would acylate such groups, at least in part, to yield dimeric or polymeric materials. Thus, when X is OH, $NH_2$ or NHalk, a reactive complex formed with carbonyldiimidazole is employed. This complex will react with ammonia or methyl or ethylamine but not with a 4-amino or 4-hydroxy group. This alternate preparative method is illustrated below.

EXAMPLE 16

Preparation of 3-(3-trifluoromethylphenyl)-4-amino-5-isothiazolecarboxamide.

One gram of 3-(3-trifluoromethylphenyl)-4-amino-5-isothiazolecarboxylic acid and 0.7 g. of carbonyldiimidazole were dissolved in 25 ml. of DMF at ambient temperature. The solution was stirred for 2.25 hours; 3 ml. of 14 N aqueous ammonium hydroxide were added and the resulting mixture stirred overnight at ambient temperature after which time it was poured into an ice-water mixture. 3-(3-Trifluoromethylphenyl)-4-amino-5-isothiazolecarboxamide formed in the above reaction precipitated and the precipitate was collected by filtration and was dried. 3-(3-Trifluoromethylphenyl)-4-amino-5-isothiazole carboxamide, thus prepared and purified, melted at about 124° C. after recrystallization from an ethyl acetate-hexane solvent mixture; yield 0.4 g.

Analysis calculated for $C_{11}H_8F_3N_3OS$. Theory: C, 45.99; H, 2.81; N, 14.63. Found: C, 46.23; H, 2.10; N, 14.73.

The preparation of starting materials useful in the synthesis of compounds according to I above are set forth below.

Preparation 1

A solution of sodium ethoxide was prepared by dissolving 4.6 g. of metallic sodium in 100 ml. of ethanol. The ethanolic solution was stirred and cooled to 0° C., in an ice bath. Thirty-seven grams of 3-trifluoromethylbenzyl cyanide was added in one portion to the cold ethanolic sodium ethoxide solution. While the reaction mixture was stirred at 0° C., 23.4 g. of isoamyl nitrite was added dropwise over thirty minutes. Following the complete addition, the reaction mixture was stored at 0° C., for twelve hours, and then the solvent was removed by evaporation under reduced pressure to provide a solid residue. The solid thus formed was suspended in 100 ml. of diethyl ether, and the suspension was filtered to give a white solid precipitate. The precipitate was azeotroped free of water with 250 ml. of toluene, and then the toluene was removed under reduced pressure to yield 36 g. of a solid product. The solid was again taken up in 200 ml. of toluene, and the reaction mixture was stirred while 28.6 g. of p-tosyl chloride was added in one portion. The reaction mixture next was heated at reflux for ten hours and then cooled to room temperature. The organic mixture was washed with water, with saturated aqueous sodium bicarbonate solution, again with water, dried, and the solvent was removed by evaporation under reduced pressure to give a solid product. The solid was crystallized from ethanol to give 27.0 g. of 3-trifluoromethyl-α-(p-toluenesulfonyloxyimino)benzylcyanide. M.P. 128°–130° C.

By following the above procedure, the following oximes were prepared from the corresponding benzylcyanides.

4-Ethoxy-α-(p-toluenesulfonyloxyimino)benzylcyanide

3-Chloro-α-(p-toluenesulfonyloxyimino)benzylcyanide. M.P. 159°–162° C.

3-Methoxy-α-(p-toluenesulfonyloxyimino)benzylcyanide

Preparation of Salts 5 g. of Methyl 3-(3-trifluoromethylphenyl)-4-amino-5-isothiazolecarboxylate were refluxed with 1.1 g. of potassium hydroxide in 25 ml. of ethanol. After the hydrolysis was complete, the reaction mixture was poured into 500 ml. of ether. The ethereal mixture was filtered and the filter cake dried to yield 4.2 g. of 3-(3-trifluoromethylphenyl)-4-amino-5-isothiazolecarboxylic acid, potassium salt melting at about 275° C. with decomposition.

Analysis calculated for $C_{11}H_6F_3N_2O_2SK$. Theory: C, 40.49; H, 1.84; N, 8.59 Found: C, 39.92; H, 2.13; N, 8.44.

2.9 g. of 3-(3-Trifluoromethylphenyl)-4-amino-5-isothiazolecarboxylic acid were dissolved in 10 ml. of 1 N aqueous sodium hydroxide; Calcium chloride hydrate (0.74 g) dissolved in 3 ml. of water was added to the solution of the sodium salt. The calcium salt of the isothiazolecarboxylic acid precipitated. 50 ml. of Ethanol were added and the reaction mixture kept at ambient temperature for one hour. The mixture was poured into a mixture of ice and water. The resulting solid was filtered and air dried. Yield was 2 g. of the monohydrate calcium salt of 3-(3-trifluoromethylphenyl)-4-amino-5-isothiazolecarboxylic acid melting above 300° C.

Analysis calculated for $C_{22}H_{12}F_6N_4O_4S_2Ca \cdot H_2O$ Theory: C, 41.77; H, 2.22; N, 8.86 Found: C, 41.31; H, 2.55; N, 8.61.

The above procedure was followed except that magnesium chloride was substituted for calcium chloride. 3-(3-Trifluoromethylphenyl)-4-amino-5-isothiazolecarboxylic acid, magnesium salt thus prepared melted above 300° C.

Analysis calculated for $C_{22}H_{12}F_6N_4O_4S_2Mg$. Theory: C, 44.13; H, 2.02; N, 9.36 Found: C, 43.85; H, 2.06; N, 9.59.

As previously stated, those compounds according to formula I above in which R is OH or OM are xanthine oxidase inhibitors in vitro. Since uric acid is produced by the oxidation of, first, hypoxanthine to xanthine and, second, of xanthine to uric acid via the enzyme, xanthine oxidase, an inhibitor of xanthine oxidase in vivo would obviously decrease the uric acid concentrations in the blood. Thus all compounds which inhibit xanthine oxidase in vitro are potential antigout drugs.

The in vitro xanthine oxidase assay was carried out according to the procedure of Kalckar, *J. Biol. Chem.,* 167, 429 (1947). Xanthine oxidase activity was measured at room temperature by the rate of uric acid formation from xanthine substrate. In a total volume of 1 ml., the incubation mixture contained 50 micromoles of potassium phosphate buffer at pH 7.4, 0.05 micromoles of xanthine and 0.01 units of enzyme preparation (chromatographically purified milk xanthine oxidase, grade III, obtained from Sigma Chemical Company, St. Louis, Mo.). The absorbence change at 292 nm was recorded by a Gilford recording spectrophotometer and the uric acid formed was calculated using an extinction coefficient of 12 mM$^{-1}$ Cm$^{-1}$ at 292 nm. The results of these assays are set forth in Tables I–IV which follow. Each table carries a structural formula at the head and the left-hand column in each table indicates the particular variations in the structural formula, while the right-hand column gives the concentration of drug in nanograms per ml. which inhibits 50% of the oxidation of xanthine to uric acid by the xanthine oxidase preparation.

TABLE 1

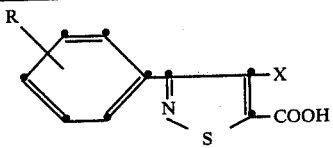

| R | R$^1$ | I$_{50}$ (nanograms/ml) |
|---|---|---|
| H | H | 470 |
| 3-CF$_3$ | H | 22 |
| 4-CF$_3$ | H | 180 |
| 3-CH$_3$ | H | 150 |
| 4-CH$_3$ | H | 280 |
| 3-OCH$_3$ | H | 290 |
| 4-OCH$_3$ | H | 140 |
| 4-OC$_2$H$_5$ | H | 28 |
| 3-Cl | H | 68 |
| 4-Cl | H | 700 |
| 3-F | H | 300 |
| 4-F | H | 380 |
| 4-Br | H | 825 |
| 3-F | 4-OCH$_3$ | 18 |
| 3-OCH$_3$ | 5-OCH$_3$ | 25 |
| 3-CH$_3$ | 4-OCH$_3$ | 40 |
| 3-OCH$_3$ | 4-OCH$_3$ | 115 |
| 3,4-methylenedioxy | | 130 |
| 3-Cl | 4-Cl | 62 |
| 4-OC$_3$H$_7$ | H | 24 |
| 4-OCH(CH$_3$)$_2$ | H | 19 |

TABLE 2

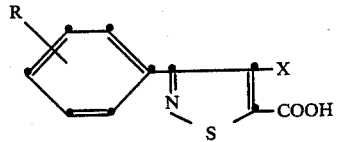

| R | X | I$_{50}$ (nanograms/ml) |
|---|---|---|
| H | Cl | 54 |
| 3-CF$_3$ | — | 10 |
| 3-OCH$_3$ | — | 29 |
| 4-OCH$_3$ | — | 14 |
| 3-CH$_3$ | — | 34 |
| 4-CH$_3$ | — | 80 |
| 3-Cl | — | 19 |
| 4-Cl | — | 100 |

TABLE 2-continued

| R | X | I$_{50}$ (nanograms/ml) |
|---|---|---|
| 3-F | — | 30 |
| 4-F | — | 52 |
| 3-CF$_3$ | Br | 18 |
| 3-Cl | — | 26 |
| 4-Cl | — | 100 |
| 3-CF$_3$ | I | 95 |
| 3-Cl | — | 330 |
| 3-OCH$_3$ | — | 620 |
| 4-Cl | — | 1000 |
| 3-CF$_3$ | F | 20 |

TABLE 3

| R | X | I$_{50}$ (nanograms/ml) |
|---|---|---|
| H | H | 480 |
| 3-CF$_3$ | — | 15 |
| 3-OCH$_3$ | — | 880 |
| 4-OCH$_3$ | — | 65 |
| 3-Cl | — | 80 |
| 4-Cl | — | 470 |
| H | OH | 45 |
| 3-CF$_3$ | — | 7.4 |
| 3-CF$_3$ | NH—CH$_3$ | 170 |

TABLE 4

| Ar | I$_{50}$ (nanograms/ml) |
|---|---|
| 3-pyridinyl | 330 |
| 2-thienyl | 750 |

All of the compounds corresponding to formula I above which applicants have prepared are active in vivo in lowering plasma uric acid levels. Two different experimental methods were used to determine in vivo activity but both methods gave comparable results. The first method, the spectrofluorometric method, was modified from the procedure of Sumi et al., *Clinica. Chimica. Acta.,* 73, 233 (1976). Rats were sacrificed by decapitation and their blood collected into vacutainer tubes containing heparin via heparinized glass funnels. The blood was centrifuged for 8 minutes at 4000 rpm after which time the plasma was separated and diluted 1:1 with water. Plasma protein was precipitated by addition of acetic acid to a final concentration of 0.007 molar and boiling the resulting mixture for 5 minutes in Sorval tubes. Clear deproteinized plasma was obtained after centrifugation of the resulting plasma for 30 minutes at 25,000 rpm. Uric acid was assayed as follows: 0.2 ml. aliquots of the clear deproteinized plasma were mixed with 120λ of uricase (0.045 mu/ml.) and incubated for 30 minutes at 27° C. 1.0 ml. of a p-hydroxyphenylacetic acid buffer was added. Samples obtained from feeding rats or dogs serial doses of the compound under test were incubated with the above buffer solution for 30 minutes at 27° C. Fluorescence of the solution was measured in quartz tubes using an Aminco Bowman-Spectrofluorimeter having excitation of 321 nm and emission at 412 nm. Five uric acid standards from 6-30 micromolar were assayed for each test and each standard yielded a linear curve.

The second method was called the HPLC-EC Detection method. Here, blood plasma was collected from rats as described above and from dogs in heparinized syringes from the cefalic vein in the forearm and centrifuged with Sure-Sep to separate plasma. Deproteinized plasma was prepared in each instance by first diluting one volume of plasma with one volume of an internal standard solution, 4 mcg./ml., and then addition of two volumes of 5% trichloroacetic acid. Standards were added to control plasma in the range of 0-8 mcg./ml. of uric acid. Samples obtained by feeding graded doses of drug under test to dogs or rats were mixed for 30 seconds and then centrifuged in an Eppendorf microcentrifuge. Supernates were diluted 1:10 in column buffer and assayed for uric acid. Internal standards used were 3-methyluric acid for the rat samples and 3,9-dimethyluric acid for dog samples. Assays were performed as follows using a Bioanalytic Systems Inc. LC-44 analyser and an electrochemical detector system based on an Altex model 110 pump coupled with a CP-O carbon paste electrodetector. Samples for assay were put into a DuPont 834 autosampler and automatically injected into a laboratory packed stainless steel column (4.1 mm id, ¼" od 25 cm.1) containing reverse phase packing (sperisorb. O.D. 5μ Regis Chemical Co.). The column buffers employed were 0.1 M disodium phosphate, 0.05 M citric acid and 10% methanol for rat samples; 0.1 M disodium phosphate, 10% methanol and citric acid titrated at pH 6.5 for dog samples. The same internal standards were employed as before. Retention times for uric acid, 3-methyluric acid and 3,9-dimethyluric acid were established. Uric acid levels were then calculated from peak areas by computer analysis. Table V which follows gives the oral $ED_{50}$ in rats for a group of the preferred compounds of this invention (those in which the 3-position of the isothiazole ring carries a 3-trifluoromethylphenyl group). In the table, column 1 gives the substituent at C-4 of the isothiazole ring and column 2 the $ED_{50}$ in mg. per kg. (that dose which reduces plasma level of uric acid by one-half).

The compounds represented by the above formula are also relatively non-toxic. In column 3 of Table V are listed the oral $LD_{50}$ for mice in mg. per kg. for each of the compounds of column 1 (dose which kills one-half of the animals). Finally, column 4 in Table V gives the ratio of $LD_{50}$ to $ED_{50}$. It will be seen that the ratio of the $LD_{50}$ to the $ED_{50}$ is quite high, giving a substantial margin of safety for using the compounds of this invention in treating gout in mammals, particularly humans.

Other compounds represented by Formula I above are also active in vivo inhibitors of xanthine oxidase. Table 6 which follows gives results obtained by the oral administration of an ester and two amides of 3-(3-trifluoromethylphenyl)-4-amino-5-isothiazolecarboxylic acid. In the table, column 1 gives the acid derivative, column 2 the dosage and column 3, the percent inhibition.

TABLE 5

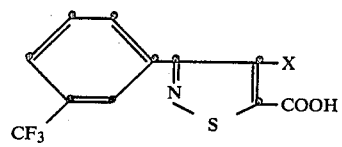

| X | $ED_{50}$ mg/kg | $LD_{50}$ mg/kg | Ratio |
|---|---|---|---|
| $NH_2$ | 17.5 | 798 ± 66 | 45.6 |
| Cl | 6.4 | 138 ± 12 | 21.6 |
| H | 15.0 | 201 ± 13 | 13.4 |
| Br | 5.2 | ≈260 | ≈50 |
| OH | 18.0 | 727 ± 35 | 40 |

TABLE 6

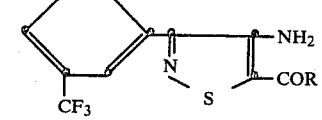

| R | Oral Dosage mg.kg | Percent Inhibition |
|---|---|---|
| $OCH_3$ | 25 | 64 |
| $NH_2$ | 50 | 13 |
| $NHCH_3$ | 25 | 32 |

The compounds represented by formula I above, since they are all active by the oral route are preferably formulated in solid form for oral administration. For example, a table containing from 100 to 250 mg. of a compound according to formula I would contain also per tablet 38 mg. starch, 25 mg. lactose, 2 mg. ethylcelluose, 7 mg. alginic acid, 1 mg. magnesium stearate and 2 mg. of talc. A formulation utilizing capsules would contain per capsule from 100 to 250 mg. or 500 mg. of compound according to formula I, 48 mg. of lactose and 2 mg. of magnesium stearate. Solid formulations for loading into capsules can be prepared with 600 or even 800 mg. of drug per dose if the drug is first densified. For parenteral administration, only the acids or non-toxic cationic salts (R=OH or OM) can be employed. If an acid is employed, it is neutralized with 10% sodium hydroxide and the resulting solution mixed with an isotonic salt solution. Preferably, a salt (compounds according to formula I in which R is OM) is employed and simply added to the isotonic salt solution in the desired injection volume.

Drugs such as those represented by Formula I above which are useful in lowering blood urate (uric acid) levels to within normal limits on oral administration are useful in treating gout (gouty arthritis) particularly when that disease is caused predominately by abnormalities in purine metabolism.

We claim:

1. A method for lowering the blood urate (uric acid) level in mammals which comprises the parenteral administration to a mammal having an elevated blood urate level and in need of treatment of a drug of the formula

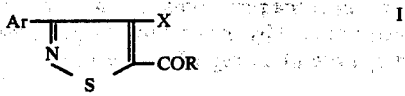

wherein
Ar is pyridyl, thienyl, phenyl or

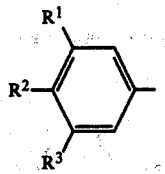

wherein at least one of $R^1$, $R^2$ and $R^3$ is H and the other two are individually H, $CF_3$, Cl, Br, F, alk or O-alk, only one of $R^1$, $R^2$ and $R^3$ can be I, or $R^1$ and $R^2$ or $R^2$ and $R^3$ when taken together are methylenedioxy;

X is $NH_2$, H, hal, OH or NH-alk;

R is OH or OM; wherein hal is Cl, F, I, or Br; alk is ($C_1$–$C_3$) alk; and M is a non-toxic cation in a quantity sufficient to lower said elevated blood urate level.

2. A method for lowering the blood urate (uric acid) level in mammals which comprises the oral administration to a mammal having an elevated blood urate level and in need of treatment of an effective amount of a drug of the formula

wherein
Ar is pyridyl, thienyl, phenyl or

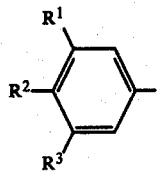

wherein at least one of $R^1$, $R^2$ and $R^3$ is H and the other two are individually H, $CF_3$, Br, Cl, F, alk or O-alk, only one of $R^1$, $R^2$ and $R^3$ can be I, or $R^1$ and $R^2$ or $R^2$ and $R^3$ when taken together are methylenedioxy;

X is $NH_2$, H, hal, OH or NH-alk;

R is OH, OM, O-alk, $NH_2$, NH-alk or N(alk)$_2$; wherein hal is Cl, F, I, or Br; alk is ($C_1$–$C_3$) alkyl; and M is a non-toxic cation; in an amount sufficient to lower said blood urate levels.

3. A method according to claim 1 in which the administered drug has the formula

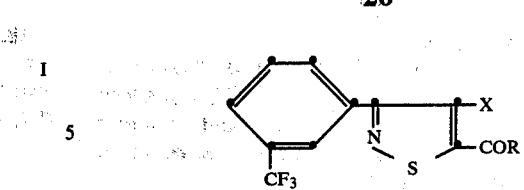

wherein X is H, OH, $NH_2$, hal or NHalk; and R is OH or OM, wherein hal is I, Br, Cl or F; alk is ($C_1$–$C_3$) alkyl and M is a non-toxic cation.

4. A method according to claim 2 in which the administered drug has the formula

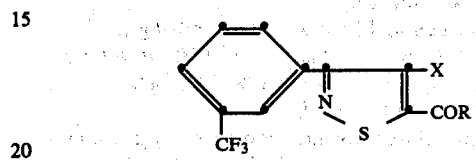

wherein X is H, OH, hal, $NH_2$ or NHalk; R is OH, OM, O-alk, $NH_2$, NHalk or N(alk)$_2$, wherein alk is ($C_1$–$C_3$) alkyl, hal is F, Cl, Br or I and M is a non-toxic cation.

5. A method according to claim 2 in which 3-(3-trifluoromethylphenyl)-4-amino-5-isothiazolecarboxylic acid or a non-toxic cationic salt thereof is administered.

6. A method according to claim 2 in which 3-(3-trifluoromethylphenyl)-4-hydroxy-5-isothiazolecarboxylic acid or a non-toxic cationic salt thereof is administered.

7. A method according to claim 2 in which 3-(3-trifluoromethylphenyl)-4-chloro-5-isothiazolecarboxylic acid or a non-toxic cationic salt thereof is administered.

8. A method according to claim 2 in which 3-(3-trifluoromethylphenyl)-4-bromo-5-isothiazolecarboxylic acid or a non-toxic cationic salt thereof is administered.

9. A method according to claim 2 in which 3-(3-trifluoromethylphenyl)-4-fluoro-5-isothiazolecarboxylic acid is a non-toxic cationic salt thereof is administered.

10. A method according to claim 2 wherein a dosage of from 2–20 mg./kg. of mammalian body weight is administered.

11. A pharmaceutical formulation in unit dosage form adapted for oral administration comprising per unit dosage an amount of a drug of the formula

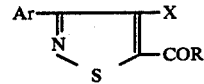

wherein
Ar is pyridyl, thienyl, phenyl or

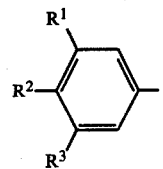

wherein at least one of $R^1$, $R^2$ and $R^3$ is H and the other two are individually H, $CF_3$, Br, Cl, F, alk or O-alk, only one of $R^1$, $R^2$ and $R^3$ can be I, or $R^1$ and $R^2$ or $R^2$ and $R^3$ when taken together are methylenedioxy;

X is $NH_2$, H, hal, OH or NH-alk;

R is OH, OM, O-alk, $NH_2$, NH-alk or $N(alk)_2$, I; wherein hal is Cl, F, I, or Br; alk is ($C_1$–$C_3$) alkyl; and M is a non-toxic cation, sufficient to lower blood urate (uric acid) levels plus one or more pharmaceutical excipients.

12. A pharmaceutical composition according to claim 11 in which the active drug is present in an amount of from 100–500 mg.

13. A pharmaceutical formulation according to claim 11 in which the active drug is 3-(3-trifluoromethylphenyl)-4-amino-5-isothiazolecarboxylic acid or a non-toxic cationic salt thereof.

14. A pharmaceutical formulation according to claim 11 in which the active drug is 3-(3-trifluoromethylphenyl)-4-hydroxy-5-isothiazolecarboxylic acid or a non-toxic cationic salt thereof.

15. A pharmaceutical formulation according to claim 11 in which the active drug is 3-(3-trifluoromethylphenyl)-4-chloro-5-isothiazolecarboxylic acid or a non-toxic cationic salt thereof.

16. A pharmaceutical formulation according to claim 11 in which the active drug is 3-(3-trifluoromethylphenyl)-4-bromo-5-isothiazolecarboxylic acid or a non-toxic cationic salt thereof.

17. A pharmaceutical formulation according to claim 11 in which the active drug is 3-(3-trifluoromethylphenyl)-4-fluoro-5-isothiazolecarboxylic acid or a non-toxic cationic salt thereof.

18. A method of inhibiting the enzyme xanthine oxidase in a mammal which comprises administering to said mammal by the oral route a xanthine oxidase inhibiting dose of a drug of the formula

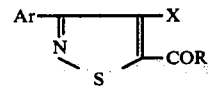

wherein

Ar is pyridyl, thienyl, phenyl or

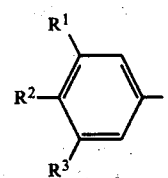

wherein at least one of $R^1$, $R^2$ and $R^3$ is H and the other two are individually H, $CF_3$, Br, Cl, F, alk or O-alk, only one of $R^1$, $R^2$ and $R^3$ can be I, or $R^1$ and $R^2$ or $R^2$ and $R^3$ when taken together are methylenedioxy;

X is $NH_2$, H, hal, OH or NH-alk;

R is OH, OM, O-alk, $NH_2$, NH-alk or $N(alk)_2$; wherein hal is Cl, F, I, or Br; alk is ($C_1$–$C_3$) alkyl; and M is a non-toxic cation.

* * * * *